US008815069B2

United States Patent
Wu et al.

(10) Patent No.: US 8,815,069 B2
(45) Date of Patent: Aug. 26, 2014

(54) DISPOSABLE CAPILLARY ELECTROPHORESIS DETECTING DEVICE

(71) Applicant: National Chung Hsing University, Taichung (TW)

(72) Inventors: Ching-Chou Wu, Taichung (TW); Yi-Tong Pan, Kaohsiung (TW)

(73) Assignee: National Chung Hsing University, Taichung (TW)

( * ) Notice: Subject to any disclaimer, the term of this patent is extended or adjusted under 35 U.S.C. 154(b) by 0 days.

(21) Appl. No.: 13/942,709

(22) Filed: Jul. 16, 2013

(65) Prior Publication Data

US 2014/0197031 A1 Jul. 17, 2014

(30) Foreign Application Priority Data

Jan. 14, 2013 (TW) .............................. 102101365 A

(51) Int. Cl.
*G01N 27/453* (2006.01)
*G01N 27/447* (2006.01)

(52) U.S. Cl.
CPC ................................ *G01N 27/44791* (2013.01)
USPC ........................................................ 204/603

(58) Field of Classification Search
CPC ................................................. G01N 27/4473
See application file for complete search history.

(56) References Cited

U.S. PATENT DOCUMENTS 6,878,255 B1    4/2005   Wang et al.

FOREIGN PATENT DOCUMENTS

TW          493623       7/2002

OTHER PUBLICATIONS

Wang et al., "Micromachined Electrophoresis Chips with Thick-Film Electrochemical Detectors," Anal. Chem. 1999, 71, 5436-5440.*
Weng-Feng Chung, "Histamine Detection by Using Capillary Electrophoretic Electrochemical (CE-EC) Chip," Master's thesis, Jul. 2010, The Graduate School, Department of BioMedical Engineering, National Cheng Kung University.
Tung-Meng Tsai, "Design and Development of Electroanalytical Methods Based on Screen Printing Technology," Doctor's thesis, Mar. 2006, The Graduate School, Department of Chemistry, National Chung Hsing University.
Castaño-Álvarez M. et al., "Amperometric detector designs for capillary electrophoresis microchips," Journal of Chromatography A, Jan. 10, 2006, pp. 291-299.

(Continued)

Primary Examiner — Alex Noguerola
(74) Attorney, Agent, or Firm — Jianq Chyun IP Office

(57) ABSTRACT

A disposable capillary electrophoresis detecting device includes a fixing device, a capillary electrophoresis microchip, and an electrochemical sensor microchip. The fixing device includes two chip-fixing bases having a first chip-holding cavity horizontally arranged and a second chip-holding cavity vertically arranged. The second chip-holding cavity is substantially perpendicular to the first chip-holding cavity and faces an end portion thereof. The capillary electrophoresis microchip is horizontally placed in the first chip-holding cavity. The electrochemical sensor microchip is vertically placed in the second chip-holding cavity. In the electrochemical sensor microchip, a patterned insulation layer is located on a detecting electrode, exposes a sensor area of the detecting electrode, and is extended to two sides of the sensor area. The outlet of the separation capillary of the capillary electrophoresis microchip is aligned to the sensor area, and the distance between the outlet and the sensor area is the thickness of the patterned insulation layer.

10 Claims, 8 Drawing Sheets

(56) References Cited

OTHER PUBLICATIONS

Chen G. et al., "Fabrication of Poly(dimethylsiloxane)-Based Capillary Electrophoresis Microchips Using Epoxy Templates," Microchimica Acta, vol. 153, Springer Journals, Feb. 1, 2006, pp. 151-158.

Cheng H. et al., "Comparison of Four Carbon Fiber Electrodes in Microfluidic Chip Integrated With Electrochemical Detector," Chinese Journal of Analytical Chemistry, vol. 36, Issue 1, Jan. 2008, pp. 1-5.

Chen S. P. et al., "Preparation of metal nanoband microelectrode on poly(dimethylsiloxane) for chip-based amperometric detection," Analytica Chimica Acta, vol. 665, Issue 2, Apr. 30, 2010, pp. 152-159.

Joseph W. et al., "Dual Conductivity/Amperometric Detection System for Microchip Capillary Electrophoresis," Analytical Chemistry, vol. 74, No. 23, Dec. 1, 2002, pp. 5919-5923.

Kovachev N. et al., "Fast and Selective Microfluidic Chips for Electrochemical Antioxidant Sensing in Complex Samples," Analytical Chemistry, vol. 82, No. 7, Apr. 1, 2010, pp. 2925-2931.

Liu A. L. et al., "Plastified poly(ethylene terephthalate) (PET)-toner microfluidic chip by direct-printing integrated with electrochemical detection for pharmaceutical analysis," Talanta, Feb. 15, 2006, pp. 1303-1308.

Manz A. et al., "Miniaturized Total Chemical Analysis Systems: a Novel Concept for Chemical Sensing," Sensors and Actuators B: Chemical, vol. 1, Issues 1-6, Jan. 1990, pp. 244-248.

Pumera M. et al., "Microchip electrophoresis with wall-jet electrochemical detector: Influence of detection potential upon resolution of solutes," Electrophoresis, Aug. 1, 2006, pp. 5068-5072.

Vandaveer W. R. et al., "Recent developments in electrochemical detection for microchip capillary electrophoresis," Electrophoresis, Nov. 2004, pp. 3528-3549.

Wang Y. et al., "A high-performance polycarbonate electrophoresis microchip with integrated three-electrode system for end-channel amperometric detection," Electrophoresis, May 2008, pp. 1881-1888.

Wendell K. T. C. et al., "Electrophoresis microchip fabricated by a direct-printing process with end-channel amperometric detection," Electrophoresis, Nov. 2004, pp. 3832-3839.

Wu Y. et al., "An end-channel amperometric detector for microchip capillary electrophoresis," Talanta, Oct. 2004, pp. 338-344.

* cited by examiner

DISPOSABLE CAPILLARY ELECTROPHORESIS DETECTING DEVICE

CROSS-REFERENCE TO RELATED APPLICATION

This application claims the priority benefit of Taiwan application serial no. 102101365, filed on Jan. 14, 2013. The entirety of the above-mentioned patent application is hereby incorporated by reference herein and made a part of this specification.

BACKGROUND OF THE INVENTION

1. Field of the Invention

The invention relates to a detecting device. More particularly, the invention relates to a disposable capillary electrophoresis detecting device where a capillary electrophoresis (CE) microchip and an electrochemical sensor microchip are integrated.

2. Description of Related Art

Capillary electrophoresis has been applied in the field of clinical medicine, food sanitation, and environmental inspection. To be specific, the clinical applications of CE mainly aim to detect neurotransmitters or molecular bioinformatics in blood or cerebrospinal fluid; as to the field pertinent to food sanitation, CE is often applied to detect pesticide residue, illegal additives, and other poisonous residues; in terms of environmental inspection, the CE technique is frequently employed to detect presence of heavy metals or environmental hormones. In general, the detecting method to which the CE technique may be applied includes an optical detecting method and an electrochemical detecting method. Since the optical detecting method requires large-sized detecting equipment and cannot be performed in a rapid manner in response to the requirement for on-the-spot inspection, the CE detecting method integrated with the electrochemical detecting method has been prevailing recently.

The high separation efficiency of the CE technique is mostly achieved by interaction between electrophoretic and electroosmotic flow (EOF) for separating the ions/molecules with positive charges, negative charges, or no charges. Due to the recent development of the lab-on-a-chip (LOC) technology, the CE capillaries may also be miniaturized on a portable microchip. Besides, the detecting method may also be adjusted in compliance with the requirement of the electrochemical sensor microchip, so as to miniaturize the entire microchip and simplify the entire detecting process.

According to the relative positions of the electrochemical electrode and the capillary channel, the electrochemical sensors integrated with the CE microchip may be categorized into the following three types: (1) the in-channel type: the working electrode is placed in the separation channel and in the separation high-voltage electric field; (2) the off-channel type: the working electrode is placed in the separation channel, and a decoupler is applied to shunt the separation high-voltage electric field, thereby eliminating the disturbance of the separation electric field to the detecting electrode; (3) the end-channel type: the working electrode is placed on the outside of the separation channel and around the outlet of the CE capillaries, either on or off chip. In the on-chip alignment mode of the end-channel detection, the electrode and the capillary separation channel are incorporated into the same substrate of the microchip; in the off-chip alignment mode, the electrode and the capillary separation channel are formed on different substrate of the microchips. In case of the in-channel detection, the off-channel detection, and the on-chip mode of the end-channel detection, the electrode and the capillary separation channel are formed together; accordingly, if it is necessary to modify the electrode, change the material of the electrode, or replace the damaged or polluted electrode, the electrode cannot be replaced individually, which leads to repetitive manufacturing and increases manufacturing costs. By contrast, the off-chip mode of the end-channel detection requires that the electrode and the capillary separation channel are formed separately and then assembled together, thus facilitating the fabrication and reducing the manufacturing costs.

Nonetheless, the integration of the off-chip type of the electrochemical sensors and the CE microchip is subject to the difficulty in aligning the outlet of the capillary of the CE microchip to the detecting electrode, and thus the off-chip type mode has not been prevalent. To be specific, the electrochemical detecting tank is far greater than the width of the CE capillary, which lessens the pushing force of the EOF; at this time, the bands of sample which are originally concentrated will be swiftly dispersed. If the outlet of the CE capillary is not aligned to the electrochemical detecting electrode, and if the distance between the outlet and the electrochemical detecting electrode is not properly monitored, the sensitivity and reproducibility of the detection will be deteriorated. A number of methods have been proposed to adjust the distance between the outlet of the CE capillary and the electrochemical detecting electrode, whereas most of these methods rely on the use of an optical microscope or a micro-positioning device. This inevitably raises the complexity of replacing the detecting electrode and also fails to comply with the real-time requirement for the on-the-spot inspection.

SUMMARY OF THE INVENTION

The invention is directed to a disposable capillary electrophoresis detecting device including a capillary electrophoresis microchip and an electrochemical sensor microchip which may be assembled with ease. Here, an outlet of the separation capillary of the capillary electrophoresis microchip is aligned to a sensor area of a detecting electrode of the electrochemical sensor microchip, and a distance between the outlet of the separation capillary and the sensor area is the thickness of an insulation layer located on the electrochemical sensor microchip.

In an embodiment of the invention, a disposable capillary electrophoresis detecting device that includes a fixing device, a capillary electrophoresis microchip, and an electrochemical sensor microchip is provided. The fixing device includes a first chip-fixing base and a second chip-fixing base. The first chip-fixing base has a first chip-holding cavity that is horizontally arranged, and the first chip-holding cavity has an end portion. The second chip-fixing base has a second chip-holding cavity that is vertically arranged. Here, the second chip-holding cavity is substantially perpendicular to the first chip-holding cavity and faces the end portion of the first chip-holding cavity. The capillary electrophoresis microchip is horizontally placed and positioned in the first chip-holding cavity, such that an edge of the capillary electrophoresis chip is substantially aligned to the end portion of the first chip-holding cavity, and the capillary electrophoresis microchip has an injection capillary, a separation capillary, and a sample tank. An outlet of the separation capillary is located at the edge of the capillary electrophoresis microchip. The electrochemical sensor microchip is vertically placed and positioned in the second chip-holding cavity. Besides, the electrochemical sensor microchip includes a substrate, a detecting electrode, and a patterned insulation layer. The detecting electrode is located on the substrate and has a sensor area. The patterned insulation layer is located on the detecting electrode. Here, the patterned insulation layer has a thickness and exposes the sensor area, and parts of the patterned insulation layer are at least extended to two sides of the sensor area. When the electrochemical sensor microchip is in contact with the edge of the capillary electrophoresis microchip, the outlet of the separation capillary of the capillary electrophoresis microchip is aligned to the sensor area of the detecting electrode of the electrochemical sensor microchip, and a distance between the outlet of the separation capillary and the sensor area is the thickness of the patterned insulation layer.

According to an embodiment of the invention, the thickness ranges from about 10 µm to about 100 µm.

According to an embodiment of the invention, the detecting electrode in the sensor area is an interdigitated electrode.

According to an embodiment of the invention, the parts of the patterned insulation layer at least extended to the two sides of the sensor area are respectively shaped as a triangle.

According to an embodiment of the invention, a center of the outlet of the separation capillary of the capillary electrophoresis microchip is aligned to a center of the sensor area of the detecting electrode of the electrochemical sensor microchip.

According to an embodiment of the invention, the capillary electrophoresis microchip further includes a sample waste liquid tank and a buffer liquid tank.

According to an embodiment of the invention, the detecting electrode further includes a power connecting area, and the power connecting area and the sensor area are respectively located at a top end and a bottom end of the detecting electrode.

According to an embodiment of the invention, the capillary electrophoresis microchip further includes a substrate and a polymer membrane located on the substrate, and the injection capillary, the separation capillary, the buffer liquid tank, the sample tank, and the sample waste liquid tank are formed in the polymer membrane.

According to an embodiment of the invention, a method of forming the first chip-fixing base and the second chip-fixing base includes laser cutting and adhesion.

According to an embodiment of the invention, the injection capillary and the separation capillary are crossed to form an intersection.

As described above, in the disposable capillary electrophoresis detecting device provided herein, the capillary electrophoresis microchip and the electrochemical sensor microchip are inserted into the first chip-holding cavity and the second chip-holding cavity, respectively, such that the outlet of the separation capillary of the capillary electrophoresis microchip is aligned to the sensor area of the detecting electrode of the electrochemical sensor microchip, and the distance between the outlet of the separation capillary and the sensor area is determined by the thickness of the insulation layer located on the electrochemical sensor microchip. Thereby, the alignment of the capillary electrophoresis microchip to the electrochemical sensor microchip and the control of the distance therebetween may be achieved without employing the microscope and the micro-positioning device, such that the use convenience, the detection sensitivity, and the measurement reproducibility of the detecting device may be significantly improved.

Several exemplary embodiments accompanied with figures are described in detail below to further describe the invention in details.

BRIEF DESCRIPTION OF THE DRAWINGS

The accompanying drawings are included to provide further understanding, and are incorporated in and constitute a part of this specification. The drawings illustrate exemplary embodiments and, together with the description, serve to explain the principles of the invention.

DETAILED DESCRIPTION OF DISCLOSED EMBODIMENTS

Figure 1A:
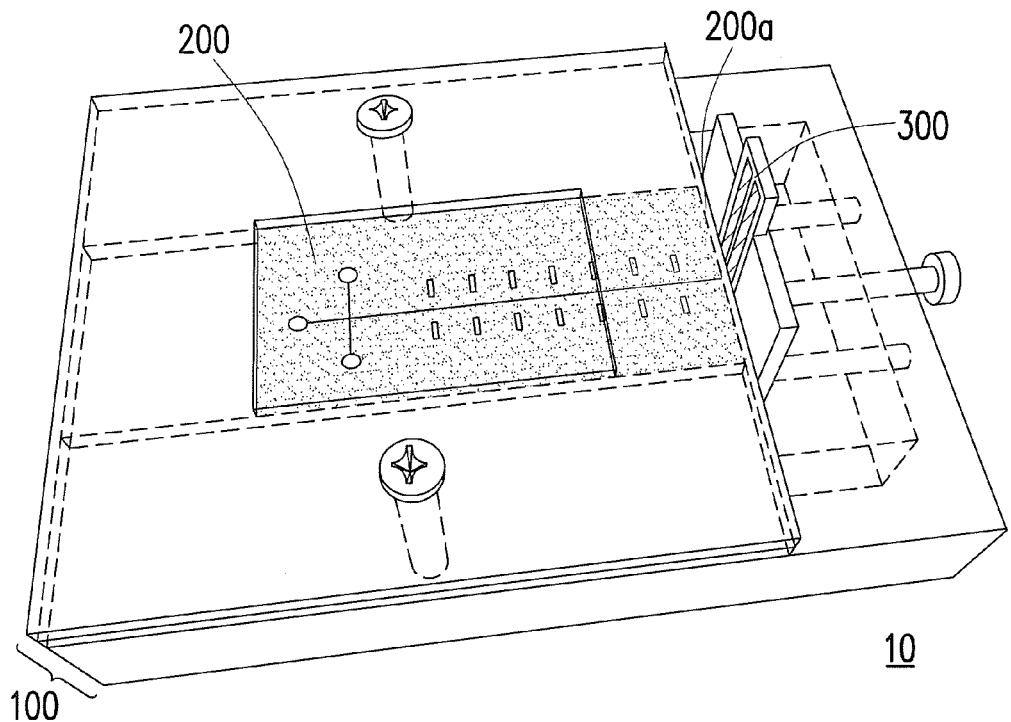
FIG. 1A is a schematic view illustrating a disposable capillary electrophoresis detecting device according to an embodiment of the invention.
Figure 1B:
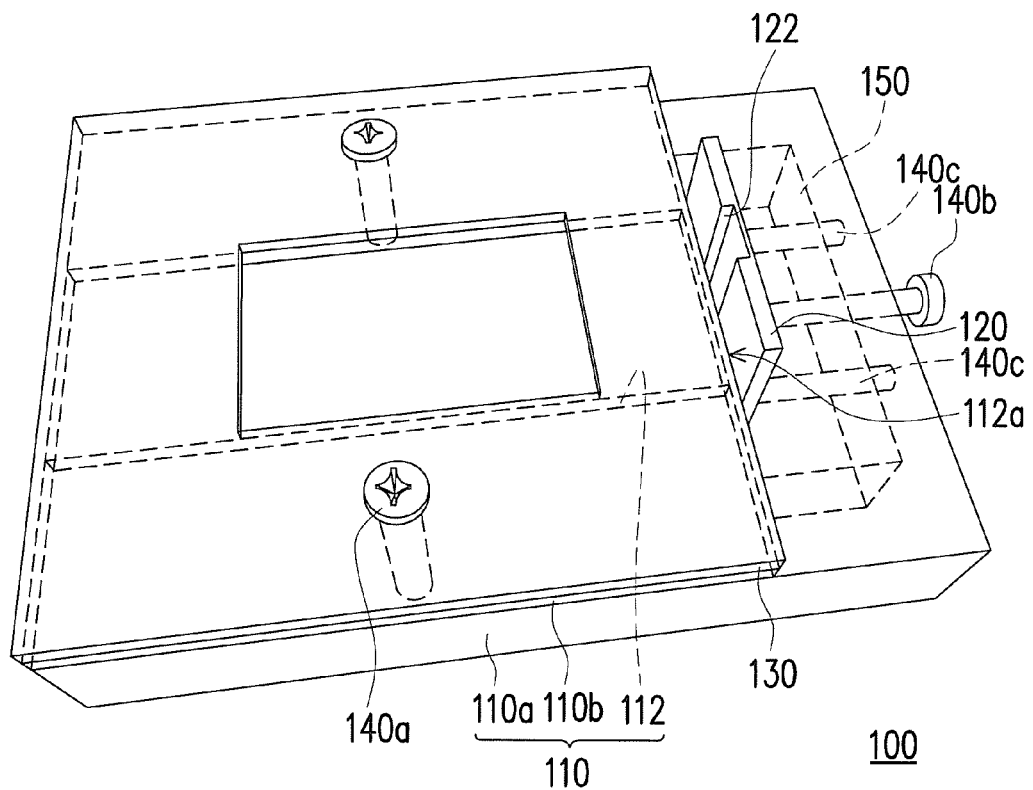
FIG. 1B is a schematic view illustrating the fixing device of FIG. 1A.
Figure 1C:
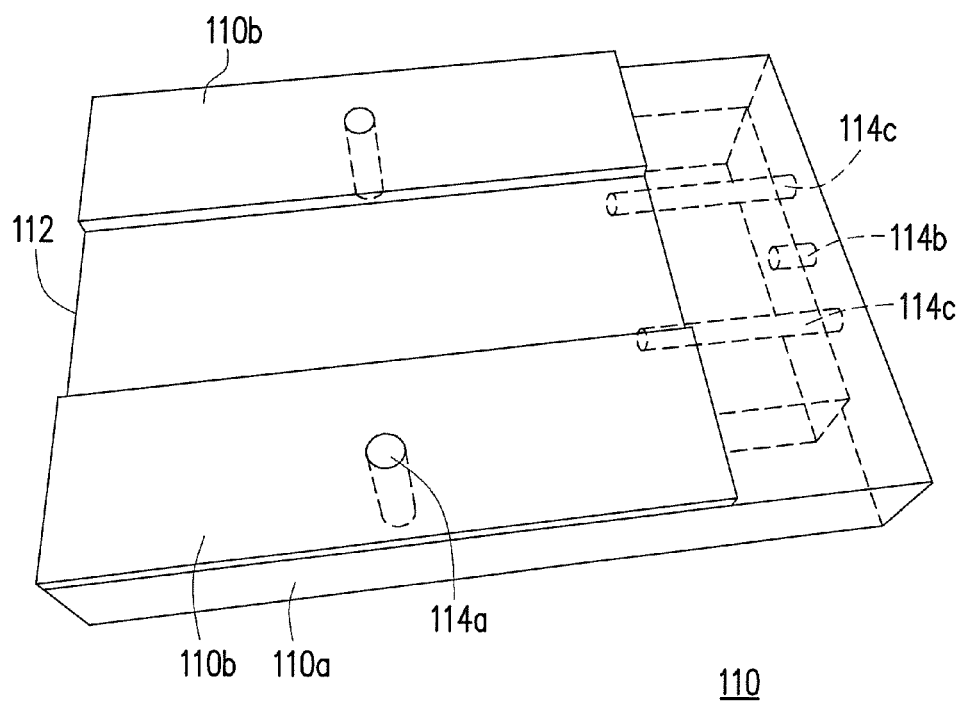
FIG. 1C is a schematic view illustrating the first chip-fixing base of FIG. 1A.

FIG. 1A is a schematic view illustrating a disposable capillary electrophoresis detecting device according to an embodiment of the invention, FIG. 1B is a schematic view illustrating the fixing device of FIG. 1A, and FIG. 1C is a schematic view illustrating the first chip-fixing base of FIG. 1A. With reference to FIG. 1A and FIG. 1B, the disposable capillary electrophoresis detecting device 10 includes a fixing device 100, a capillary electrophoresis microchip 200, and an electrochemical sensor microchip 300. The fixing device 100 includes a first chip-fixing base 110 and a second chip-fixing base 120. The first chip-fixing base 110 has a first chip-holding cavity 112 that is horizontally arranged, and the first chip-holding cavity 112 has an end portion 112a. Particularly, the first chip-fixing base 110 includes a base 110a and two plates 110b disposed on two sides of the base 110a, and the first chip-holding cavity 112 is formed by the base 110a and the plates 110b, for instance. In addition, the first chip-fixing base 110 has holes 114a, 114b and 114c. The second chip-fixing base 120 has a second chip-holding cavity 122 that is vertically arranged. Moreover, the second chip-fixing base 120 has holes (not shown) disposed corresponding to the holes 114c. Here, the second chip-holding cavity 122 is substantially perpendicular to the first chip-holding cavity 112 and faces the end portion 112a of the first chip-holding cavity 112. In the present embodiment, the fixing device 100 may be referred to as a clamping device, the first chip-fixing base 110 is horizontally arranged, and the second chip-fixing base 120 is vertically arranged, for instance. The fixing device 100 further includes a top cover 130, fixing members 140a and 140b, and rails 140c, for instance. The top cover 130 is arranged on the first chip-fixing base 110 and has an opening that exposes a portion of the first chip-holding cavity 112. The fixing members 140a and 140b are screws, for instance. Here, the fixing members 140a are screwed into the holes 114a, and serve to secure the top cover 130, and the first chip-fixing base 110, for instance, such that the capillary electrophoresis microchip 200 may be fixed into the first chip-holding cavity 112 located between the top cover 130 and the first chip-fixing base 110. The rails 140c are slid into the holes 114c and the holes of the second chip-fixing base 120 to hold the second chip-fixing base 120 in a horizontal position relative the first chip-fixing base 110. The fixing member 140b is inserted into the hole 114b, and serves to fix the second chip-fixing base 120 to one side of the first chip-fixing base 110, for instance, such that the relative positions of the first and second chip-fixing bases 110 and 120 remain unchanged, and that the electrochemical sensor microchip 300 may be in contact with the capillary electrophoresis microchip 200. For example, the hole 114b having a female section (not shown) and the fixing member 140b having a male section (not shown) are matched and engaged when the second chip-fixing base 120 is pushing forward by the fixing member 140b. In the meantime, the two sides of the second chip-fixing base 120 are fixed by the rails 140c. In addition, the fixing device 100 further includes a waste liquid tank 150 that is located below the second chip-fixing base 120 and used to collect waste liquid (e.g., detection liquid, buffer liquid, and so forth).

According to the present embodiment, the first chip-fixing base 110, the second chip-fixing base 120, and other components are made of acrylic, for instance, and a method of forming the first chip-fixing base 110 including the base 110a and plates 110b, the second chip-fixing base 120, and other components includes laser cutting, adhesion, and so on. For instance, the shape of the to-be-cut component is depicted with use of illustration software (e.g., AutoCAD), and the resultant image file is output to the machine (e.g., the carbon dioxide laser processing machine) characterized by high cutting precision. The acrylic material is then cut by the laser processing machine, and the surface of the cut component is polished and planarized by means of the milling machine or other tools according to actual requirements. A small amount of organic solvent (e.g., acetone) is then applied to dissolve parts of the components where the adhesion process is to be performed, and certain force is exerted to adhere the components to each other. Based on actual requirements, it is likely to additionally fill in the seams between the components with adhesives, such as thermal adhesives, AB adhesives, and so on. Thereby, the first chip-fixing base 110, the second chip-fixing base 120, and other components may have precise dimension and they are mutually matched.

Figure 2:
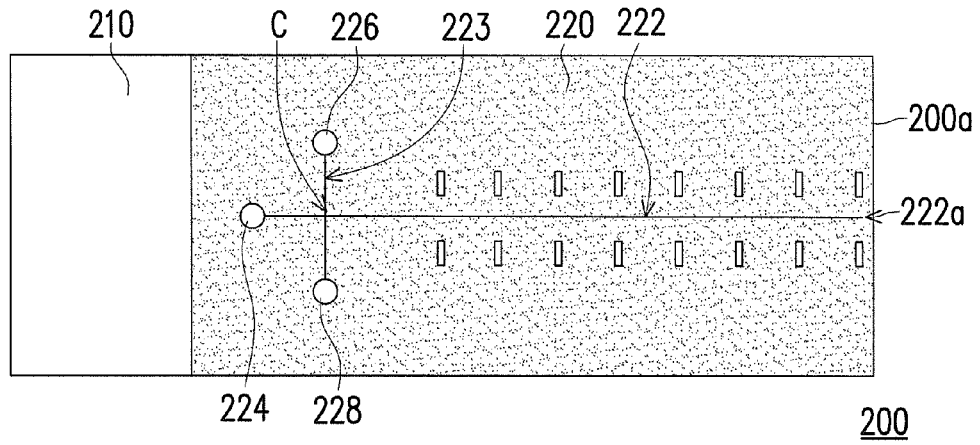
FIG. 2 is a schematic view illustrating the capillary electrophoresis microchip of FIG. 1A.

FIG. 2 is a schematic view illustrating the capillary electrophoresis microchip of FIG. 1A. With reference to FIG. 1A and FIG. 2, the capillary electrophoresis microchip 200 is horizontally placed and positioned in the first chip-holding cavity 112, such that an edge 200a of the capillary electrophoresis chip 200 is substantially aligned to the end portion 112a of the first chip-holding cavity 112. The capillary electrophoresis microchip 200 has an injection capillary 223, a separation capillary 222 and a sample tank 228, and an outlet 222a of the separation capillary 222 is located at the edge 200a of the capillary electrophoresis microchip 200. In the present embodiment, the capillary electrophoresis microchip 200 includes a substrate 210 and a polymer membrane 220 that is located on the substrate 210. The polymer membrane 220 includes the separation capillary 222, the injection capillary 223, the sample tank 228, the sample waste tank 226, and the buffer liquid tank 224 formed in the polymer membrane 220. Here, the separation capillary 222 is substantially formed between the buffer liquid tank 224 and the edge 200a of the capillary electrophoresis microchip 200.

In the present embodiment, the substrate 210 is a glass substrate that is cut by the machine (e.g., the carbon dioxide laser cutting machine) characterized by high cutting precision, for instance, and the glass substrate may have precise dimension and smooth edges. The polymer membrane 220 is made of a material suitable for electrophoretic separation, e.g., polydimethylsioxane (PDMS). The injection capillary 223 is disposed between the sample waste liquid tank 226 and the sample tank 228. The separation separation capillary 222 is disposed between the edge 200a of the capillary electrophoresis chip 200 and the buffer liquid tank 224. The separation separation capillary 222 and the injection capillary 223 are crossed to form an intersection C. The width of the separation capillary 222 and the injection capillary 223 ranges from about 10 µm to about 150 µm, e.g., 60 µm; the height of the separation capillary 222 and the injection capillary 223 ranges from about 10 µm to about 150 µm, e.g., 26 µm. The distance between the intersection C and the sample tank 228, the distance between the intersection C and the sample waste liquid tank 226, and the distance between the intersection C and the buffer liquid tank 224 are equal, e.g., 5 mm. The distance between the intersection C and the outlet 222a of the separation capillary 222 ranges from about 10 mm to about 100 mm, e.g., 45 mm. Certainly, the invention is not limited thereto; for instance, several rectangular patterns are often formed on the polymer membrane 220, and the distance between every two of the rectangular patterns is 5 mm, for instance. According to the desired length of the separation capillary 222, the polymer membrane 220 may be cut along the rectangular patterns, so as to obtain the capillaries with different lengths.

Figure 3:
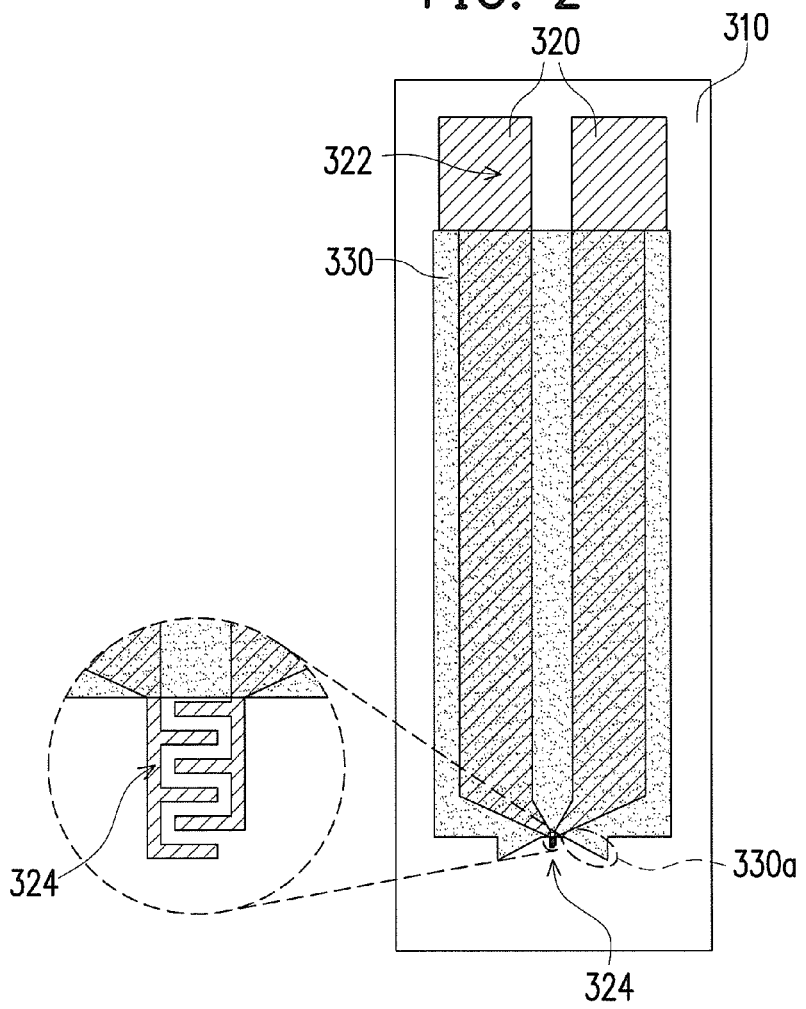
FIG. 3 is a schematic view illustrating the electrochemical sensor microchip of FIG. 1A.

FIG. 3 is a schematic view illustrating the electrochemical sensor microchip of FIG. 1A. With reference to FIG. 1A and FIG. 3, the electrochemical sensor microchip 300 is vertically placed and positioned in the second chip-holding cavity 122. The electrochemical sensor microchip 300 includes a substrate 310, a detecting electrode 320, and a patterned insulation layer 330. In the present embodiment, the substrate 310 is made of glass, for instance. The detecting electrode 320 is located on the substrate 310 and has a power connecting area 322 and a sensor area 324. In the present embodiment, the power connecting area 322 and the sensor area 324 are respectively located at a top end and a bottom end of the detecting electrode 320. Here, the detecting electrode 320 may have the electrochemical detecting capability and may be shaped in various manner. A material of the detecting electrode 320 is gold, for example. According to the present embodiment, the detecting electrode 320 includes a pair of bar-shaped electrodes, and the bar-shaped electrodes 320 in the sensor area 324 are interdigitated electrodes, for instance. The width and the distance between the interdigitated electrodes are about 20 μm, respectively, and the length of the interdigitated electrodes is about 90 μm, for instance. Although the detecting electrode 320 herein includes a pair of bar-shaped electrodes, and the detecting electrode 320 in the sensor area 324 refers to the interdigitated electrode, the invention is not limited thereto. That is, the structure, the shape, the width, and the length of the detecting electrode 320 are not limited in the invention.

The patterned insulation layer 330 has a thickness t and is located on the detecting electrode 320. Besides, the patterned insulation layer 330 exposes the sensor area 324, and parts of the patterned insulation layer 330 are at least extended to two sides of the sensor area 324. In the present embodiment, the patterned insulation layer 330 is formed by coating the substrate 310 with the insulation layer having the thickness t, and the insulation layer is patterned to expose the power connecting area 322 and the sensor area 324 of the detecting electrode 320. That is, the patterned insulation layer 330 defines the sensor area 324 of the detecting electrode 320. According to the present embodiment, the parts 330a of the patterned insulation layer at least extended to the two sides of the sensor area 324 are respectively shaped as a triangle, for instance, which should however not be construed as a limitation to the invention. Namely, as long as the patterned insulation layer 330 exposes the sensor area 324 and is extended to the two sides of the sensor area 324, the patterned insulation layer 330 falls within the scope of the invention, and the shape of the parts of the patterned insulation layer 330 at least extended to the two sides of the sensor area 324 is not limited herein. In the present embodiment, the patterned insulation layer 330 is made of photoresist, for instance, and the thickness t of the patterned insulation layer 330 ranges from about 10 μm to about 100 μm, for instance.

With reference to FIG. 1A and FIG. 1B, in the present embodiment, the method of assembling the disposable capillary electrophoresis detecting device 10 exemplarily includes following steps. The fixing device 140a for fixing the first chip-fixing base 110 is loosened. The capillary electrophoresis microchip 200 is placed into the first chip-holding cavity 112, such that the edge 200a (i.e., the outlet 222a of the separation capillary 222) of the capillary electrophoresis chip 200 is substantially aligned to the end portion 112a of the first chip-holding cavity 112. The fixing member 140a is slightly locked into the first chip-fixing base 110, so as to somewhat fix the capillary electrophoresis chip 200. The electrochemical sensor microchip 300 is then inserted into the second chip-holding cavity 122 of the second chip-fixing base 120. The fixing member 140b is applied to push the second chip-fixing base 120 forward, such that the electrochemical sensor microchip 300 approaches and is adhered to the edge 200a of the capillary electrophoresis chip 200.

Figure 4A:
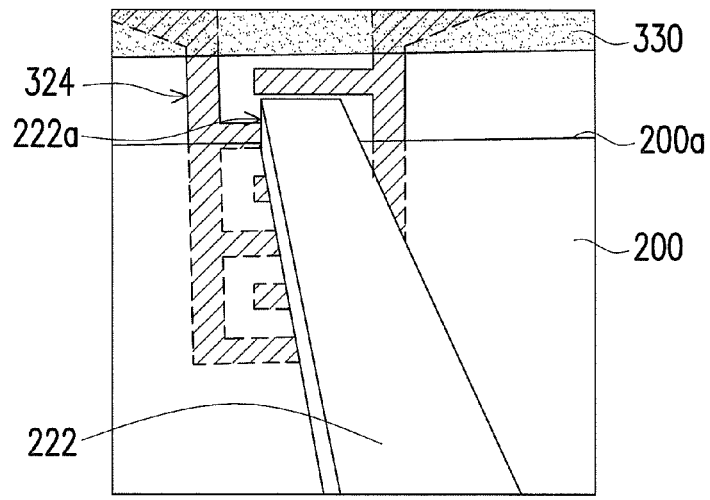
FIG. 4A is a schematic view of aligning the outlet of the separation capillary of the capillary electrophoresis microchip shown in FIG. 1A to a sensor area of a detecting electrode of an electrochemical sensor microchip.
Figure 4B:
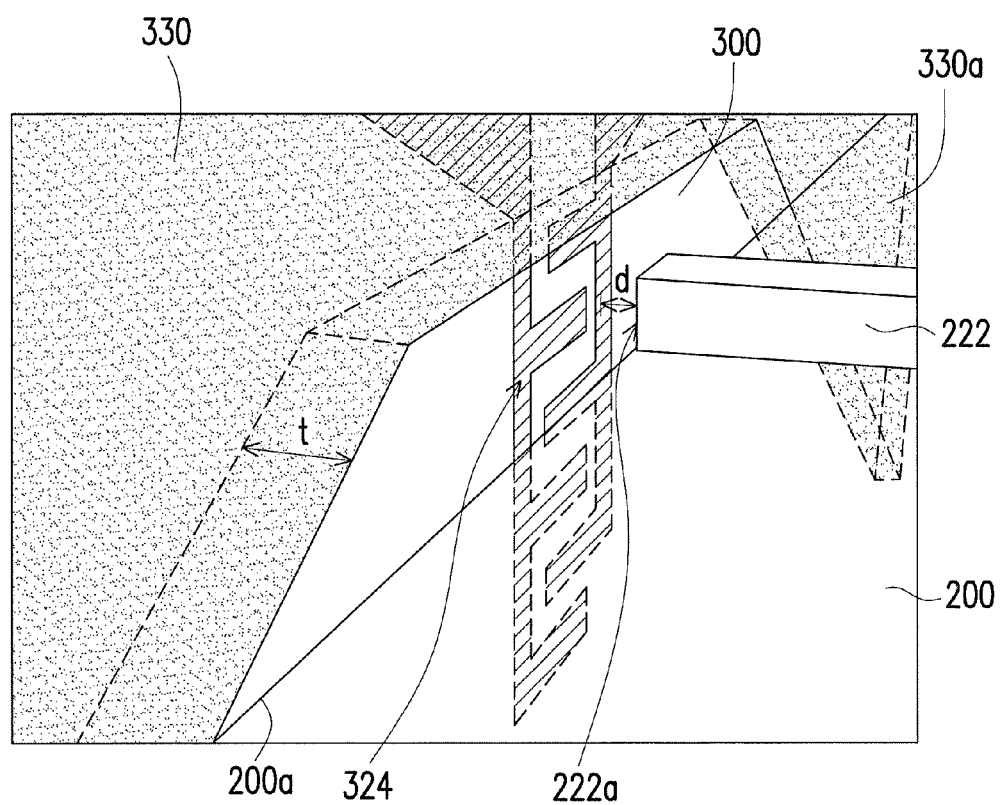
FIG. 4B is a schematic view of aligning the outlet of the separation capillary of the capillary electrophoresis microchip shown in FIG. 1A to a sensor area of a detecting electrode of an electrochemical sensor microchip.

FIG. 4A and FIG. 4B are schematic views of aligning the outlet of the separation capillary of the capillary electrophoresis shown in FIG. 1A to the sensor area of the detecting electrode of the electrochemical sensor microchip. FIG. 4A shows the alignment in a direction from the outlet of the separation capillary to the detecting electrode, and FIG. 4B is a side view illustrating the distance between the outlet of the separation capillary and the detecting electrode. In order to clearly depict the relative positions of the outlet of the separation capillary and the detecting electrode, only the separation capillary in the capillary electrophoresis microchip is illustrated, and other parts of the capillary electrophoresis microchip are omitted. With reference to FIG. 4A and FIG. 4B, when the electrochemical sensor microchip 300 is in contact with the edge 200a of the capillary electrophoresis microchip 200, the outlet 222a of the separation capillary 222 of the capillary electrophoresis microchip 200 is aligned to the sensor area 324 of the detecting electrode 320 of the electrochemical sensor microchip 300, and the distance d between the outlet 222a of the separation capillary 222 and the sensor area 324 is the thickness t of the patterned insulation layer 330. Particularly, in the present embodiment, the dimensions of the first chip-holding cavity 112, the second chip-holding cavity 122, the capillary electrophoresis microchip 200, and the electrochemical sensor microchip 300 are substantially precise and mutually matched; therefore, after the capillary electrophoresis microchip 200 and the electrochemical sensor microchip 300 are inserted into the first chip-holding cavity 112 and the second chip-holding cavity 122, the outlet 222a of the separation capillary 222 of the capillary electrophoresis microchip 200 is spontaneously aligned to the sensor area 324 of the detecting electrode 320 of the electrochemical sensor microchip 300. Here, a center of the outlet 222a of the separation capillary 222 of the capillary electrophoresis microchip 200 is exemplarily aligned to a center of the sensor area 324 of the detecting electrode 320, and the center of the sensor area 324 of the detecting electrode 320 is located between the uppermost pair of interdigitated electrodes, for instance. In addition, due to the substantially precise and mutually matched dimensions of the first chip-holding cavity 112, the second chip-holding cavity 122, the capillary electrophoresis microchip 200, and the electrochemical sensor microchip 300, favorable repeatability may be achieved when the capillary electrophoresis microchip 200 and the electrochemical sensor microchip 300 are assembled to the fixing device 100. Thereby, the variance caused by replacing the microchip may be diminished.

On the other hand, when the electrochemical sensor microchip 300 is pushed forward by the fixing member 140b and is then fixed to the edge 200a of the capillary electrophoresis microchip 200, the parts 330a of the patterned insulation layer extended to the two sides of the sensor 324 of the electrochemical sensor microchip 300 are pushed against the edge 200a of the capillary electrophoresis microchip 200. Therefore, the distance d between the capillary electrophoresis microchip 200 and the electrochemical sensor microchip 300 is directly defined by the thickness t of the patterned insulation layer 330 foamed on the detecting electrode 320. Thanks to the triangular extended parts 330a of the of the patterned insulation layer, the liquid flowing from the outlet 222a of the separation capillary 222 of the capillary electrophoresis microchip 200 is not accumulated onto the detecting electrode 320, such that the detection liquid may be spread to the waste liquid tank 150.

In the present embodiment, due to the precise and mutually matched dimensions of the fixing device 100, the capillary electrophoresis microchip 200, and the electrochemical sensor microchip 300 as well as the design of the patterned insulation layer 330 in the electrochemical sensor microchip 300, the capillary electrophoresis microchip 200 and the electrochemical sensor microchip 300, after being in contact with each other, may be spontaneously aligned to each other, and the distance between the capillary electrophoresis microchip 200 and the electrochemical sensor microchip 300 may stay unchanged. That is, in the disposable capillary electrophoresis detecting device 10, the capillary electrophoresis microchip 200 and the electrochemical sensor microchip 300 are inserted into the first chip-holding cavity 112 and the second chip-holding cavity 122 respectively and are in contact with each other. This simple process allows the outlet 222a of the separation capillary 222 of the capillary electrophoresis microchip 200 to be aligned to the sensor area 324 of the detecting electrode 320 of the electrochemical sensor microchip 300, and the distance d between the outlet 222a of the separation capillary 222 and the sensor area 324 is determined by the thickness t of the patterned insulation layer 330 located on the electrochemical sensor microchip 300. Thereby, the alignment of the capillary electrophoresis microchip 200 to the electrochemical sensor microchip 300 and the control of the distance therebetween may be achieved without employing the microscope and the micro-positioning device. That is, in the disposable capillary electrophoresis detecting device 10 described in the present embodiment, the capillary electrophoresis microchip 200 and the electrochemical sensor microchip 300 may be assembled rapidly, thus complying with the requirement for swiftly replacing the detecting electrode 320 in case of the on-the-spot inspection as well as the plug-and-play requirement. Accordingly, the use convenience, the detection sensitivity, and the measurement reproducibility of the disposable capillary electrophoresis detecting device 10 may be significantly ameliorated.

Besides, it is not necessary to employ a columnar, single-disc-shaped, and expensive microelectrode as the detecting electrode 320; instead, the interdigitated electrode which is conducive to redox cycling of electroactive substance may be applied as the detecting electrode. Hence, the manufacturing costs of the disposable capillary electrophoresis detecting device 10 may be considerably lowered down, and the detection sensitivity of the disposable capillary electrophoresis detecting device 10 may be improved. As a result, the disposable capillary electrophoresis detecting device 10 may be extensively applied to separation and detection of medicine, protein, nucleic acids, or the like.

Figure 5A:
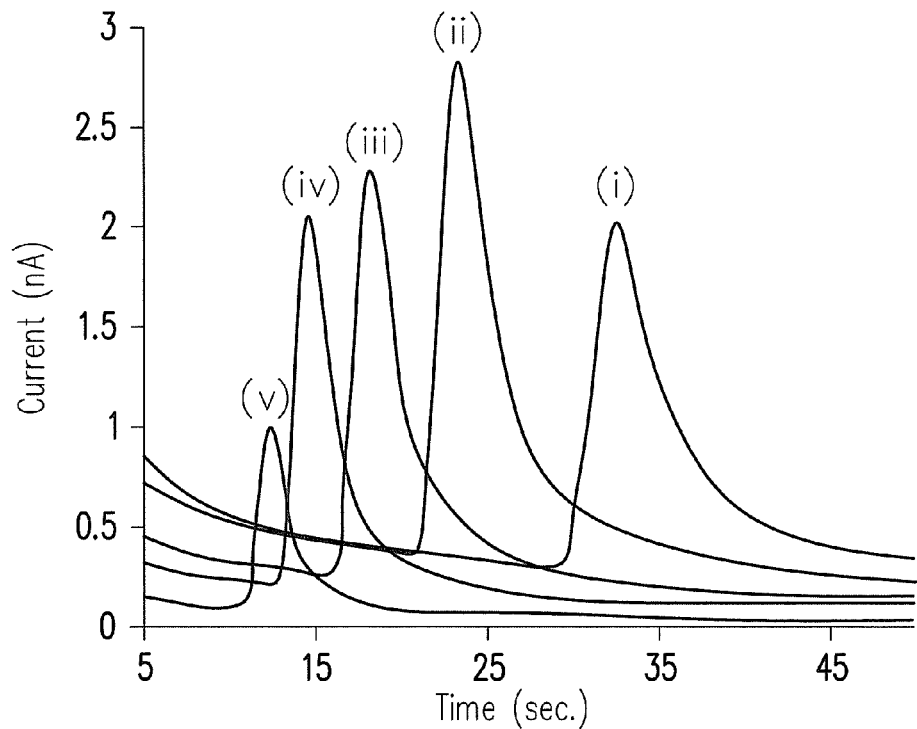
FIG. 5A and FIG. 5B are electropherograms illustrating separation of dopamine in different driving electric fields by a disposable capillary electrophoresis detecting device according to an embodiment of the invention.
Figure 5B:
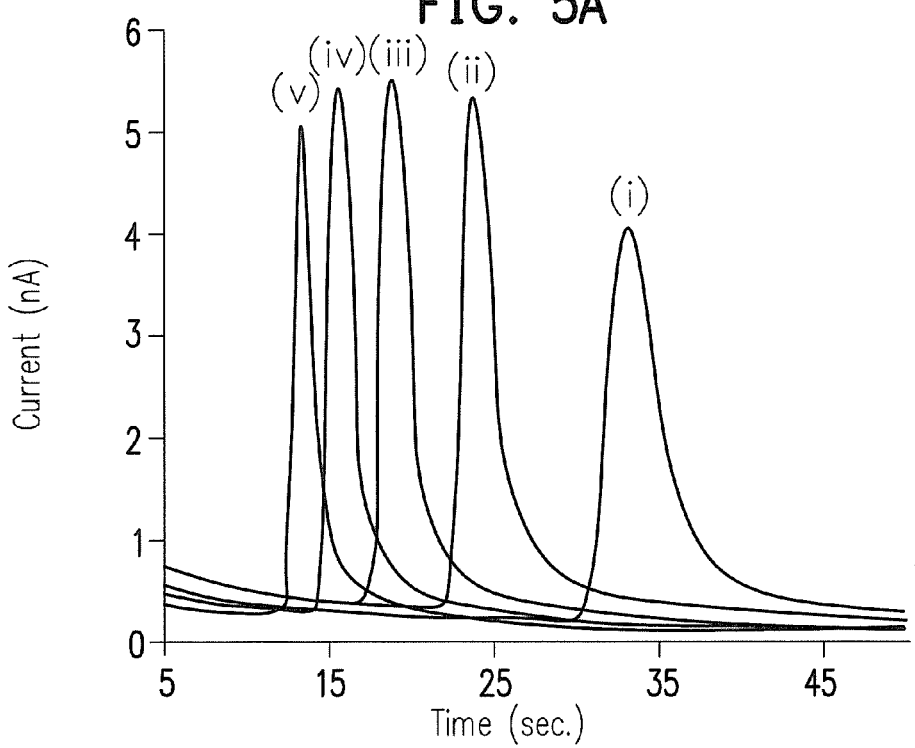

The applicability of the disposable capillary electrophoresis detecting device is explained in the following embodiments. FIG. 5A and FIG. 5B are electropherograms illustrating separation of dopamine in different driving electric fields by a disposable capillary electrophoresis detecting device according to an embodiment of the invention. The distance between the capillary electrophoresis microchip and the electrochemical sensor microchip in FIG. 5A and FIG. 5B are about 30 μm and about 10 μm, respectively; curves (i) to (v) represent that the driving electric fields respectively applied to the capillary electrophoresis microchip are (i)100 V/cm, (ii)150 V/cm, (iii)200 V/cm, (iv)250 V/cm, and (v)300 V/cm; the time frame during which the sample dopamine is injected is 3.5 seconds; the electric field for sample injecting and the electric field provided with pull-back voltage are 280 V/cm and 84 V/cm; the electric field provided with pull-back voltage is 70% of the separation electric field; the potential of the detecting electrode relative to that of a reference electrode (Ag/AgCl) is 0.7 V; the concentration of the to-be-separated dopamine is 200 μM. It can be learned from FIG. 5A and FIG. 5B that the disposable capillary electrophoresis detecting device is able to effectively separate the sample dopamine in different driving electric fields, provided that the distance between the capillary electrophoresis microchip and the electrochemical sensor microchip is about 30 μm or about 10 μm. Namely, the distance between the capillary electrophoresis microchip and the electrochemical sensor microchip in the disposable capillary electrophoresis detecting device may vary, and the disposable capillary electrophoresis detecting device may be operated when different driving electric fields are given.

Figure 6:
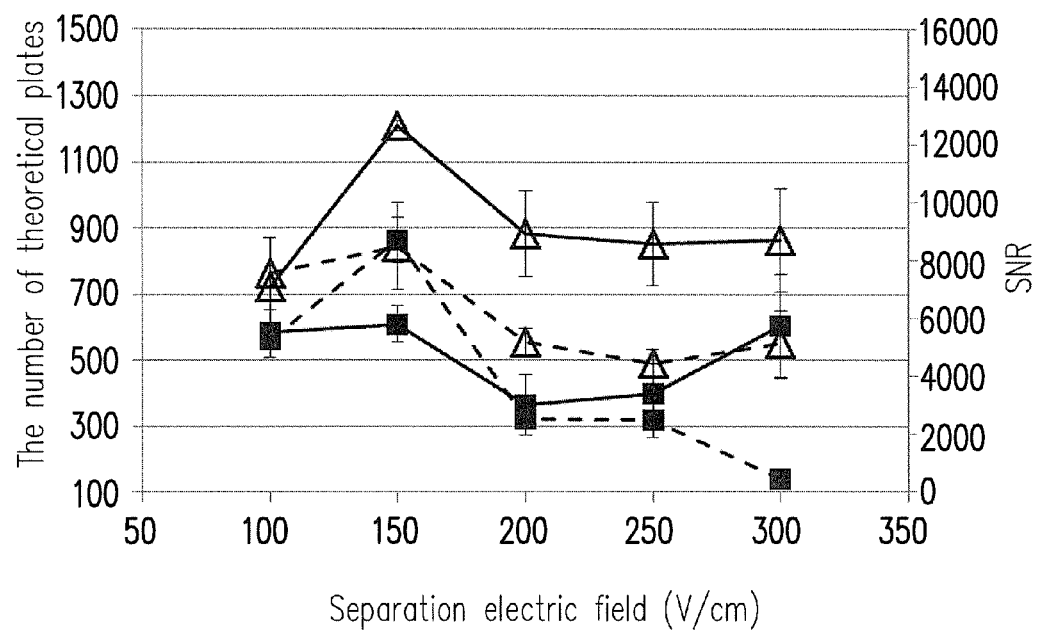
FIG. 6 is a line chart illustrating the number of theoretical plates and a signal-to-noise ratio (SNR) obtained when a disposable capillary electrophoresis detecting device is applied in different separation electric fields according to an embodiment of the invention.

FIG. 6 is a line chart illustrating the number of theoretical plates and a signal-to-noise ratio (SNR) obtained when a disposable capillary electrophoresis detecting device is applied in different separation electric fields according to an embodiment of the invention. The solid lines refer to the number of theoretical plates, the dotted lines denote the SNR, and the solid squares and the hollow triangles represent the respective distance (30 μm and 10 μm) between the capillary electrophoresis microchip and the electrochemical sensor microchip. As illustrated in FIG. 6, when the separation electric field is 150 V/cm, and the distance between the capillary electrophoresis microchip and the electrochemical sensor microchip is 10 μm or 30 μm, the resultant number of theoretical plates and the resultant SNR are relatively satisfactory. Besides, the number of theoretical plates obtained when said distance is 10 μm are greater than that obtained when said distance is 30 μm. However, the SNR obtained when said distance is 10 μm is insignificant different from that obtained when said distance is 30 μm.

Figure 7A:
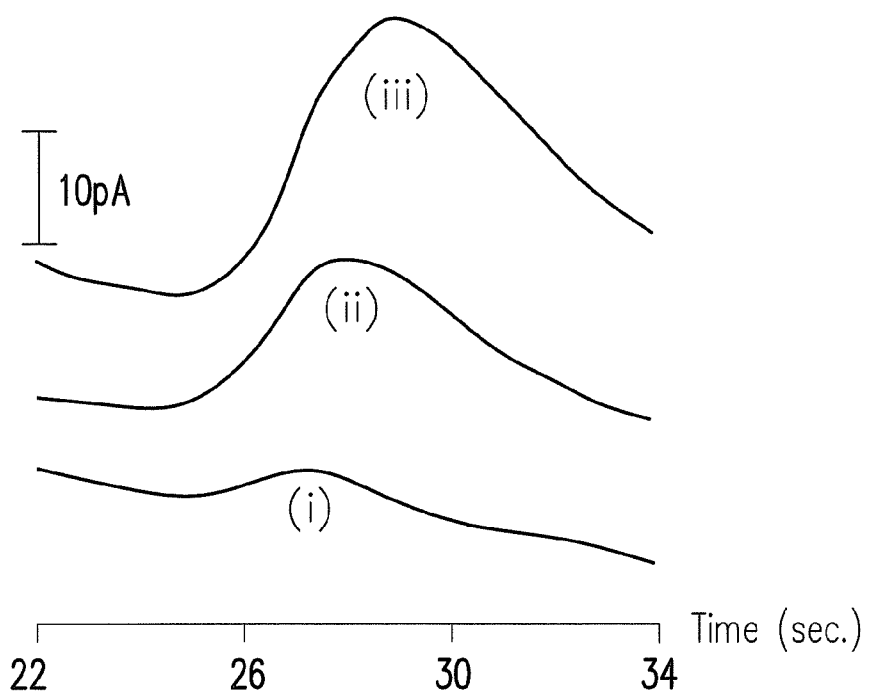
FIG. 7A is an electropherogram illustrating detection of dopamine in different concentrations by means of a disposable capillary electrophoresis detecting device according to an embodiment of the invention.
Figure 7B:
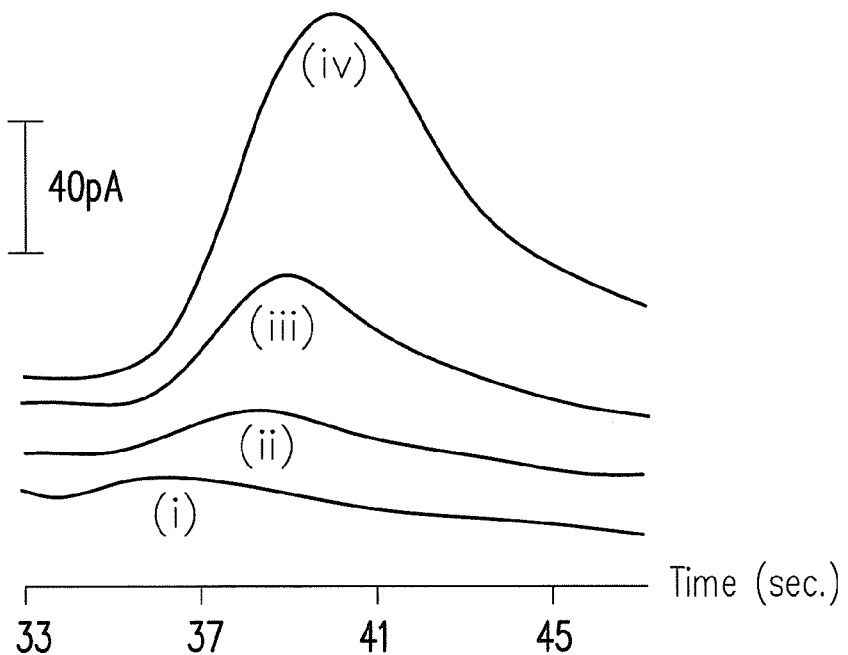
FIG. 7B is an electropherogram illustrating detection of catechol in different concentrations by means of a disposable capillary electrophoresis detecting device according to an embodiment of the invention.

FIG. 7A and FIG. 7B are electropherograms illustrating detection of dopamine and catechol in different concentrations by means of a disposable capillary electrophoresis detecting device according to an embodiment of the invention. Here, the distance between the capillary electrophoresis microchip and the electrochemical sensor microchip is about 10 μm; curves (i) to (iv) represent that the concentration of dopamine or the concentration of catechol is (i)1 μM, (ii)2 μM, (iii)5 μM, and (iv)10 μM, respectively. As shown in FIG. 7A and FIG. 7B, the linear range and the lower detection limit of the dopamine detection by means of the disposable capillary electrophoresis detecting device are 1-100 μM and 250 nM, respectively; the linear range and the lower detection limit of the catechol detection by means of the disposable capillary electrophoresis detecting device are 1-200 μM and 157 nM, respectively. That is, the disposable capillary electrophoresis detecting device is suitable for detecting different substance and may obtain favorable linear results within the proper concentration range.

Figure 8A:
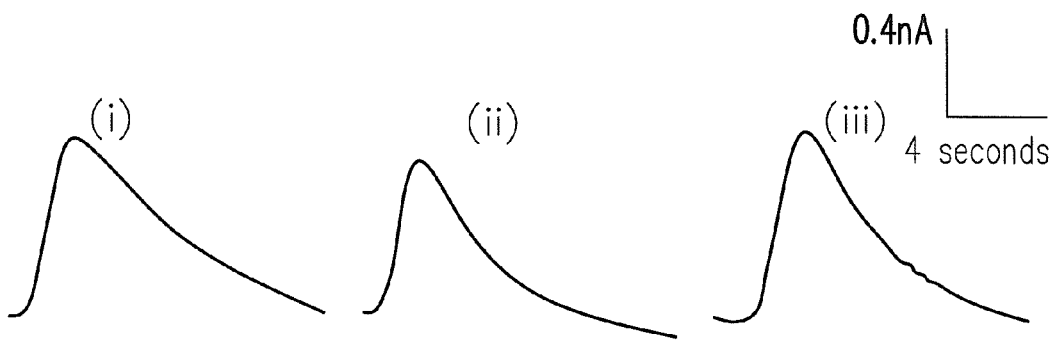
FIG. 8A is an electropherogram illustrating the use of an electrochemical sensor microchip A of a disposable capillary electrophoresis detecting device in a plug-and-play manner and a reproducibility evaluation of said use according to an embodiment of the invention.
Figure 8B:
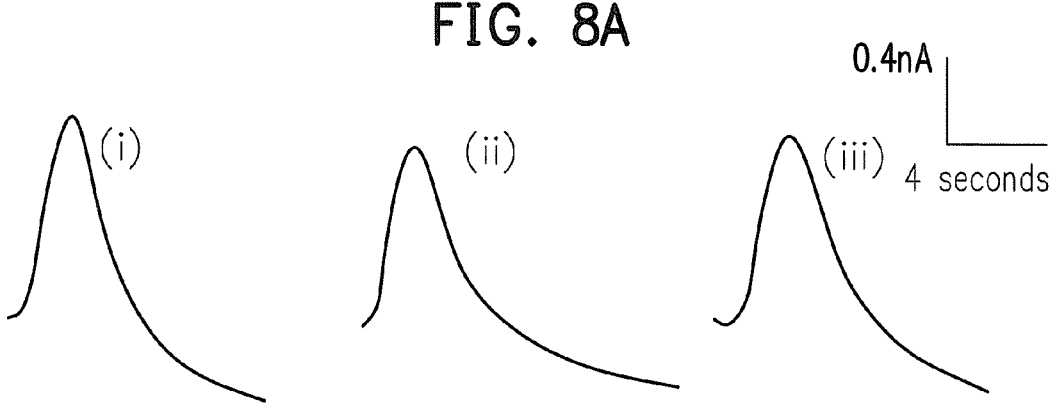
FIG. 8B is an electropherogram illustrating the use of an electrochemical sensor microchip B of a disposable capillary electrophoresis detecting device in a plug-and-play manner and a reproducibility evaluation of said use according to an embodiment of the invention.
Figure 8C:
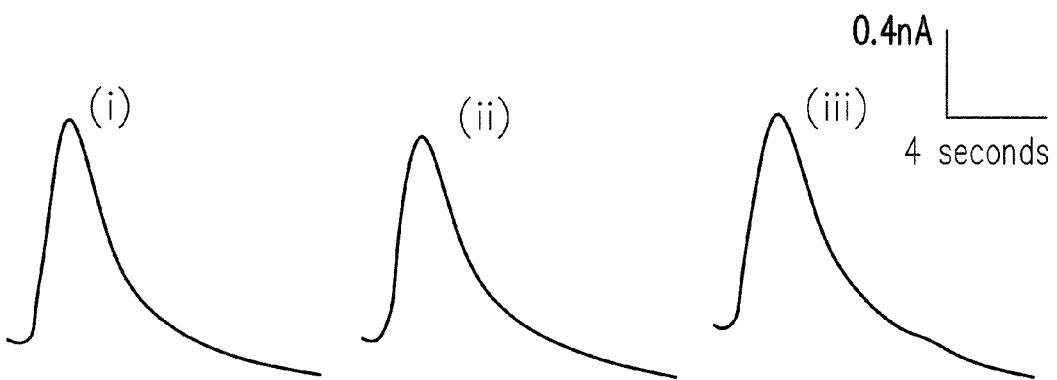
FIG. 8C is an electropherogram illustrating the use of an electrochemical sensor microchip C of a disposable capillary electrophoresis detecting device in a plug-and-play manner and a reproducibility evaluation of said use according to an embodiment of the invention.

FIG. 8A to FIG. 8C are electropherograms illustrating the use of respective electrochemical sensor microchips A, B, and C of a disposable capillary electrophoresis detecting device in a plug-and-play manner and a reproducibility evaluation of said use according to an embodiment of the invention. In particular, three microchips (i.e., A, B, and C) are provided, and a separation process is performed on the injected sample with use of the same microchip for three times, so as to obtain the separation wave peaks (i) to (iii) shown in FIG. 8A to FIG. 8C. Each microchip is immediately taken out right after each measurement and is reassembled into the fixing device after the microchip is cleansed. The average values obtained by means of the three different electrochemical sensor chips A, B, and C are analyzed. The average value acquired by performing three repetitive measurements of the electrochemical sensor chip A is 0.805±0.066 nA; the average value acquired by performing three repetitive measurements of the electrochemical sensor chip B is 0.881±0.048 nA; the average value acquired by performing three repetitive measurements of the electrochemical sensor chip C is 0.996±0.074 nA; the relative standard deviation resulting from the analysis of the electrochemical sensor chip A, the analysis of the electrochemical sensor chip B, and the analysis of the electrochemical sensor chip C is 7.0% in average. The average with the standard deviation of the peak values of the three different electrochemical sensor chips A, B, and C is 0.894±0.096 nA, and the relative standard deviation resulting from the analysis of the three electrochemical sensor chips A, B, and C is 10.8%. As discussed above, the detecting method performed by means of the disposable capillary electrophoresis detecting device described in an embodiment of the invention may accomplish favorable reproducibility.

To sum up, in the disposable capillary electrophoresis detecting device described herein, the capillary electrophoresis microchip and the electrochemical sensor microchip are inserted into the first chip-holding cavity and the second chip-holding cavity, respectively, such that the outlet of the separation capillary of the capillary electrophoresis microchip is aligned to the sensor area of the detecting electrode of the electrochemical sensor microchip, and the distance between the outlet of the separation capillary and the sensor area is determined by the thickness of the insulation layer located on the electrochemical sensor microchip. That is, due to the precise and mutually matched dimensions of the fixing device, the capillary electrophoresis microchip, and the electrochemical sensor microchip as well as the design of the patterned insulation layer in the electrochemical sensor microchip, the capillary electrophoresis microchip and the electrochemical sensor microchip may be easily aligned to each other without employing any microscope nor any micro-positioning device, and the distance between the capillary electrophoresis microchip and the electrochemical sensor microchip may be properly monitored. Thereby, the use convenience, the detection sensitivity, and the measurement reproducibility of the disposable capillary electrophoresis detecting device may be significantly improved, and the manufacturing costs of the disposable capillary electrophoresis detecting device can be considerably lowered down. Moreover, the disposable capillary electrophoresis detecting device where the capillary electrophoresis microchip and the electrochemical sensor microchip are integrated is characterized by compactness and portability, and the disposable capillary electrophoresis detecting device is able to rapidly separate the sample. In addition, the disposable capillary electrophoresis detecting device may comply with the requirement for swiftly replacing the detecting electrode in case of the on-the-spot inspection as well as the plug-and-play requirement. Accordingly, the disposable capillary electrophoresis detecting device may be extensively applied to separation and detection of medicine, protein, nucleic acids, or the like.

It will be apparent to those skilled in the art that various modifications and variations can be made to the structure of the disclosed embodiments without departing from the scope or spirit of the disclosure. In view of the foregoing, it is intended that the disclosure cover modifications and variations of this disclosure provided they fall within the scope of the following claims and their equivalents.

What is claimed is:

1. A disposable capillary electrophoresis detecting device comprising:
   a fixing device comprising:
      a first chip-fixing base having a first chip-holding cavity horizontally arranged, the first chip-holding cavity having an end portion; and
      a second chip-fixing base having a second chip-holding cavity vertically arranged, the second chip-holding cavity being substantially perpendicular to the first chip-holding cavity and facing the end portion of the first chip-holding cavity;
   a capillary electrophoresis microchip horizontally placed and positioned in the first chip-holding cavity, such that an edge of the capillary electrophoresis microchip is substantially aligned to the end portion of the first chip-holding cavity, the capillary electrophoresis microchip having an injection capillary, a separation capillary and a sample tank, wherein an outlet of the separation capillary is located at the edge of the capillary electrophoresis microchip; and
   an electrochemical sensor microchip vertically placed and positioned in the second chip-holding cavity, the electrochemical sensor microchip comprising:
      a substrate;
      a detecting electrode located on the substrate, the detecting electrode having a sensor area; and
      a patterned insulation layer located on the detecting electrode, the patterned insulation layer having a thickness and exposing the sensor area, at least parts of the patterned insulation layer at least being extended to two sides of the sensor area,
   wherein when the electrochemical sensor microchip is in contact with the edge of the capillary electrophoresis microchip, the outlet of the separation capillary of the capillary electrophoresis microchip is aligned to the sensor area of the detecting electrode of the electrochemical sensor microchip, and a distance between the outlet of the separation capillary and the sensor area is the thickness of the patterned insulation layer.

2. The disposable capillary electrophoresis detecting device as recited in claim 1, wherein the thickness ranges from about 10 μm to about 100 μm.

3. The disposable capillary electrophoresis detecting device as recited in claim 1, wherein the detecting electrode in the sensor area is an interdigitated electrode.

4. The disposable capillary electrophoresis detecting device as recited in claim 1, wherein the parts of the patterned insulation layer at least extended to the two sides of the sensor area are respectively shaped as a triangle.

5. The disposable capillary electrophoresis detecting device as recited in claim 1, wherein a center of the outlet of the separation capillary of the capillary electrophoresis microchip is aligned to a center of the sensor area of the detecting electrode of the electrochemical sensor microchip.

6. The disposable capillary electrophoresis detecting device as recited in claim 1, wherein the capillary electrophoresis microchip further comprises a sample waste liquid tank and a buffer liquid tank.

7. The disposable capillary electrophoresis detecting device as recited in claim 6, wherein the capillary electrophoresis microchip further comprises a substrate and a polymer membrane located on the substrate, and the injection capillary, the separation capillary, the buffer liquid tank, the sample tank, and the sample waste liquid tank are formed in the polymer membrane.

8. The disposable capillary electrophoresis detecting device as recited in claim 1, wherein the detecting electrode further comprises a power connecting area, and the power connecting area and the sensor area are respectively located at a top end and a bottom end of the detecting electrode.

9. The disposable capillary electrophoresis detecting device as recited in claim 1, wherein a method of forming the first chip-fixing base and the second chip-fixing base comprises laser cutting and adhesion.

10. The disposable capillary electrophoresis detecting device as recited in claim 1, wherein the injection capillary and the separation capillary are crossed to form an intersection.

* * * * *